United States Patent [19]

Guderian

[11] Patent Number: 5,350,416
[45] Date of Patent: Sep. 27, 1994

[54] APPARATUS FOR TREATMENT OF TOXINS RECEIVED FROM SNAKE BITES AND THE LIKE

[75] Inventor: Ronald H. Guderian, Port Angeles, Wash.

[73] Assignee: Venomex, Inc., Seattle, Wash.

[21] Appl. No.: 811,329

[22] Filed: Dec. 20, 1991

Related U.S. Application Data

[63] Continuation of Ser. No. 277,459, Nov. 23, 1988, Pat. No. 5,074,305, which is a continuation of Ser. No. 72,864, Jul. 14, 1987, abandoned.

[51] Int. Cl.⁵ .............................................. A61N 1/18
[52] U.S. Cl. ....................................... 607/72; 361/232
[58] Field of Search ................... 128/419 R, 421, 422, 128/783, 795, 796, 800, 803; 604/20; 361/232; 607/21, 72

[56] References Cited

U.S. PATENT DOCUMENTS

| 3,998,459 | 12/1976 | Henderson et al. | 128/419 R |
| 4,120,305 | 10/1978 | Rhoads et al. | 128/422 |
| 4,580,570 | 4/1986 | Sarrell et al. | 128/421 |

Primary Examiner—Ruth S. Smith
Attorney, Agent, or Firm—Jensen & Puntigam

[57] ABSTRACT

The apparatus includes a circuit (18) for generating an electrical signal with a sufficiently high voltage to overcome the skin resistance of the toxin victim, so that an electrical current is produced in the body area affected with the toxin. The electrical signal is applied to the site of the toxin (12) by means of a probe (14). A grounding plate (16) is positioned opposite from the toxin site (12). If the electrical signal is applied within a relatively short time following the receipt of the toxin, neutralization of the harmful effects of the toxin occurs.

4 Claims, 2 Drawing Sheets

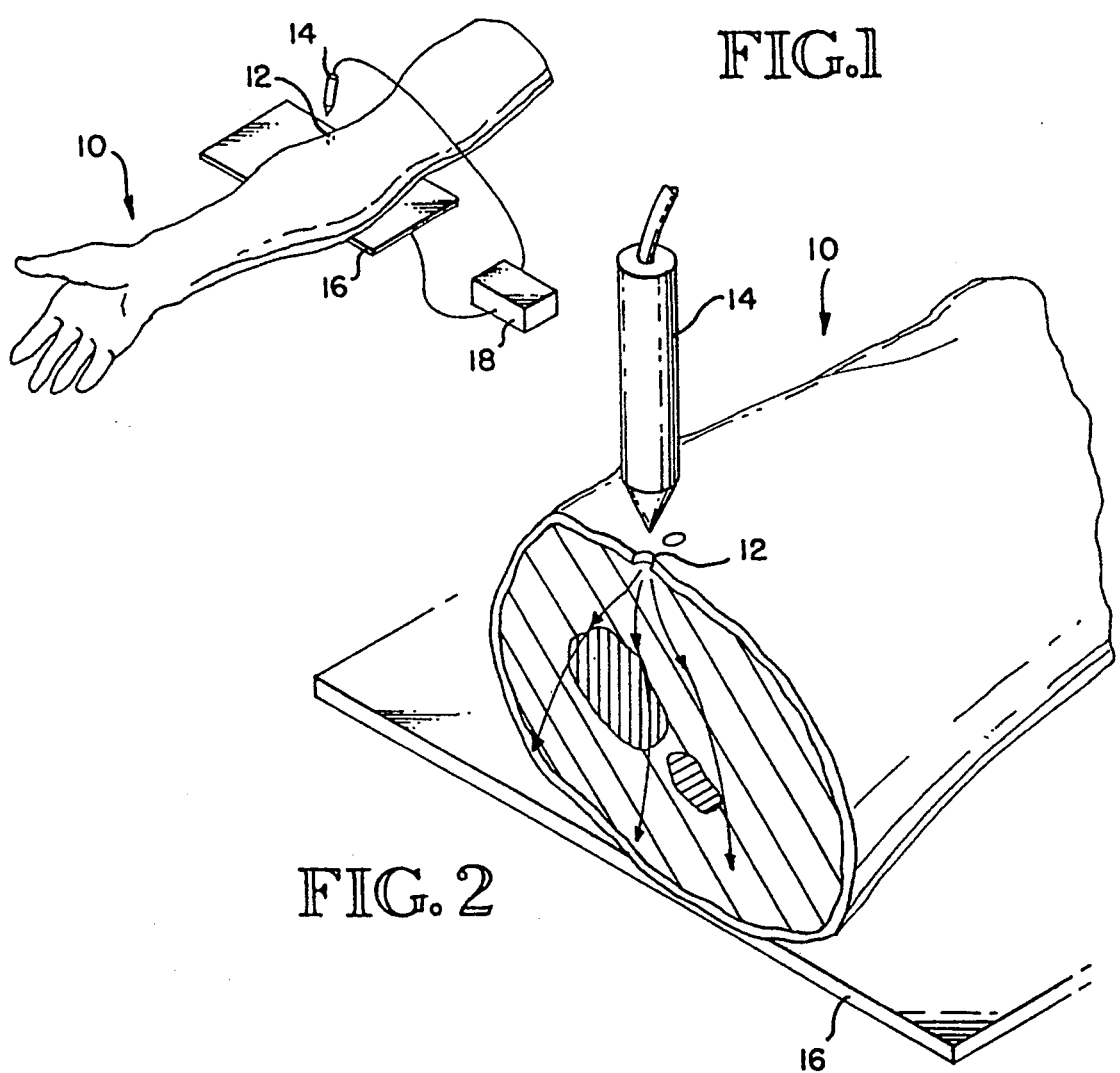

APPARATUS FOR TREATMENT OF TOXINS RECEIVED FROM SNAKE BITES AND THE LIKE

This is a continuation of application Ser. No. 277,459 filed Nov. 23, 1988, now U.S. Pat. No. 5,074,305 which in turn was a continuation of application Ser. No. 072,864, filed on Jul. 14, 1987, now abandoned.

TECHNICAL FIELD

This invention relates generally to the treatment of toxins received by virtue of venomous bites, including snake bites, bee stings and the like, as well as a result of bacterial or chemical action, and more particularly concerns an apparatus and a corresponding method which includes means for generating and applying an electric current to the victim of the toxin, typically in the vicinity of the location of the toxin.

BACKGROUND ART

It is well known that snake venom, as well as venom of other animals and some insects, is in many cases dangerous to humans, as well as animals, and can cause a variety of symptoms when injected into the body by means of fangs, stingers or the like. These symptoms range from slight discomfort, with localized skin swelling and discoloration, to severe pain and swelling, including at the extreme, possible loss of limbs due to gangrene and even death.

A number of snakes manufacture dangerous venom, including the pit viper and bushmaster in South America, and the cobra, which is found primarily in India. The venom of such snakes is sufficiently strong and complex to be dangerous to all humans as well as animals. Many insects also manufacture venom which is harmful to a certain portion of the population. Among such insects and animals are bees, certain ants, spiders, scorpions and certain sea creatures. While the venom of many of such insects has a harmful effect to some extent on nearly everyone, a relatively small part of the population may be seriously affected by the venom of certain of such insects/animals. For instance, in the United States, it has been estimated that approximately twenty percent of the population has some sensitivity to bee stings. Severe or systemic reaction, often referred to as an anaphylactic reaction which involves the respiratory functions, is found in a smaller percentage of the population.

In any event, treatment of venomous bites, including bee stings and other more serious venomous bites, is a significant health issue in the United States, even if the most dangerous venomous sources, such as the bushmaster, are not found here.

There are several recognized methods for treatment of venomous bites. Injections of selected chemicals are typically used to treat bee stings, while for snake bites, an anti-venin serum is often used. With respect to snake bites in particular, another accepted method of treatment, and in some cases now preferred, includes cutting of the bite site to promote bleeding and then removal of the venom by a sucking action.

However, it is well known that such treatment methods, particularly those involving serums, are not completely effective, particularly for snake bites, and are typically quite expensive and subject to the prompt availability of the serum. Such methods of course are typically unavailable in remote areas.

In order to solve these problems, without the use of serums or other injected substances, applicant's invention, as disclosed herein, includes the application of an electric current which is typically applied to the site of the bite wound.

Electricity has in the past been used to treat various diseases or disfunctions of the body with varying success. Applicant is aware of U.S. Pat. No. 3,991,770 to Leveen, U.S. Pat. No. 4,292,980 to Suzuki, and U.S. Pat. No. 2,771,554 to Gratzel, which are illustrative of the use of electricity, and the corresponding effects of electricity such as the production of heat, for medical treatment purposes. However, to the best of applicant's knowledge, there are no references which teach using an electric current to treat venomous bites, such as from a snake, insect or the like.

DISCLOSURE OF THE INVENTION

Accordingly, the present invention includes an apparatus and method for treatment of toxins present in an affected area of the body, including generating an electrical signal having sufficient voltage to produce a current in the affected area/tissues of the body where the toxin is present and applying the electrical signal to the body in such a manner that current moves through the affected area of the body, causing the substantial neutralization of the harmful effects of the toxin.

BRIEF DESCRIPTION OF THE DRAWINGS

FIG. 1 is a schematic view illustrating the apparatus and method of treatment of the present invention as applied to a human limb.

FIG. 2 is a schematic view showing a portion of FIG. 1 in more detail.

BEST MODE FOR CARRYING OUT THE INVENTION

Figure 3:
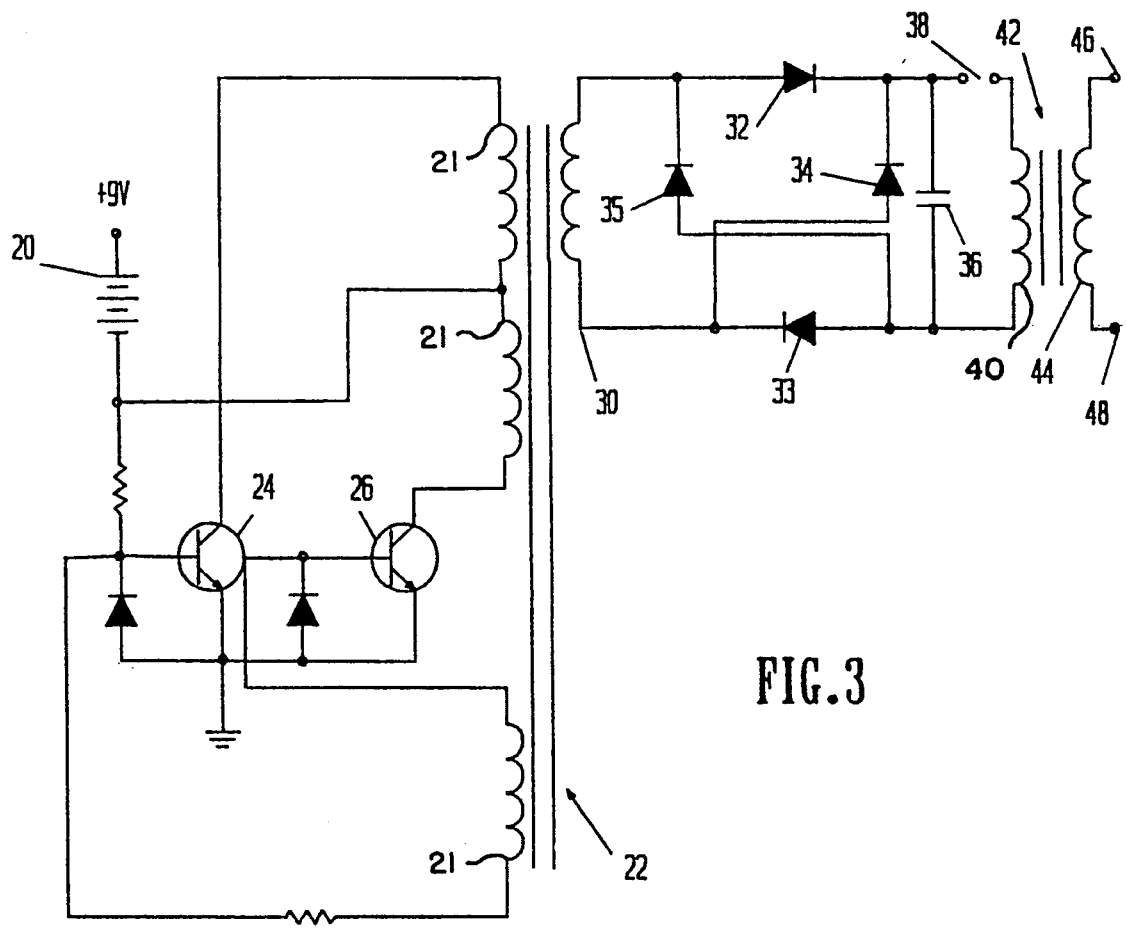
FIG. 3 is a simplified electrical diagram of one embodiment of the electric current generating portion of the apparatus of the present invention.

As indicated above, venomous bites present a danger to humans as well as animals. The results can be as severe as death or loss of a limb from highly toxic venoms, or relatively moderate such as acute swelling and discoloration, with substantial pain and fever, or relatively slight, such as minor discoloration with minimal pain and relatively localized swelling.

Typically, venom is injected into the body by a bite, which typically is characterized by a single localized area, usually on the extremities such as a limb. This is particularly true in the case of snake bites. However, with other kinds of insects, such as bees, the bites could be on the head, face and the remainder of the body, as well. Also in the case of bees, multiple bites, such as from a swarm of bees, are common. Other toxic substances in addition to animal/insect venom may be produced in the body by a bacterial infection of one kind or another, such as what typically happens in a boil, or even may be the result of humanly induced or created substances such as bacterial, biological or chemical agents introduced into the body by injection, breathing or the like, such as might occur in chemical, biological or bacterial warfare. The word toxins is used herein to cover all such substances, including particularly venom from snake bites and the like.

In the case of venomous snake bites but also with other toxins, the effect of the venom usually depends upon the amount of the venom injected as well as the toxicity and complexity of the venom itself. In some cases, such as for certain snake bites, the chemical composition of the venom is very complex, with some venoms comprising up to ten or even more different toxic substances. Such toxic substances will include a large number, i.e. as many as 26, different enzymes, many of which are found in all venoms. Typically, the complex chemical compounds in such venoms act in some manner on the membranes of the body, disturbing their function as well as their organization, resulting in the range of symptoms discussed above. In many cases only a small amount of venom can produce a very significant result. Fortunately, in many cases, the time of contact between the victim and the snake/insect is minimal, so that the amount of injected venom is relatively small and the resulting effect is not nearly as great as would be the case with a large dose.

With certain other kinds of bites, such as bees, ants and the like, the venom is much less complex and not as toxic. However, it is well recognized that a fairly large percentage of the population has developed a substantial sensitivity to such venoms, and thus, severe reactions may in fact occur in an individual person, even for a venom which on an objective scale may not be particularly toxic.

FIGS. 1 and 2 illustrate generally the method of treatment of the present invention. It should be understood that although the following description is directed toward venomous bites, the treatment could be used for other toxins as well. Assuming that the venomous bite occurs on a limb, as represented by the numeral 10, an electrical signal is applied to the site 12 of the bite by means of the combination of a probe 14, which is generally applied in the vicinity of the site 12, and a grounding plate 16 which is typically positioned on the rear side of the limb 10 opposite from the probe 14. The probe could be pointed to maximize current density or relatively blunt or rounded to cover a larger area. Also two probes, positioned near the site of toxin or across the affected area or limb could be used in some cases, as opposed to the combination of a probe and grounding plate.

The probe 14 and the grounding plate 16 are connected to an electrical signal apparatus 18. The electrical signal apparatus 18 is designed to produce an electrical current having selected characteristics. In the embodiment shown, the signal is in the form of a pulsating DC, wherein the respective pulses decay from their peak value over a selected time interval. In one particular embodiment, the output signal has a relatively high peak voltage, approximately 20 kilovolts to 50 kilovolts (open circuit), but a relatively small current, on the order of 5 milliamps or even lower. The voltage must be sufficient to overcome the skin resistance of the bite victim, as well as any clothing involved, so that an electrical current path is completed. However, once the electrical current has been established through the body, the voltage will drop to a relatively nominal value, on the order of 5–10 volts.

Although the one embodiment, which is described in more detail below and shown in FIG. 3, has a relatively high open circuit voltage, it should be understood that if a saline solution or other highly conductive solution or gel is applied to the skin prior to the application of the probe and the grounding plate, such a high open circuit voltage is not required. The voltage could in fact be relatively low, on the order of 50 volts or in some cases even lower. However, the voltage must in each circumstance be sufficient to establish and maintain the electrical current through the affected body area, such as a limb. High current levels are apparently not necessary, and so low currents, i.e. on the order of 10ma or even less, are typically used, to prevent the undesirable side effects of burning or necrosis of the skin tissues. In addition to the gel, the probe could be sharp enough to penetrate the skin, which would bring the source of electric current closer to the affected tissues.

In the one embodiment, the output signal is a pulsating DC, in which the individual pulses decay over a selected period of time. The pulse width in this embodiment is approximately 4 milliseconds. The duty cycle is approximately five percent although this could be varied substantially. It is also possible that a conventional AC current, or perhaps even a direct current (DC) could be used and accomplish similar results.

The required electrical signal can be produced by a variety of known circuits. For instance, the electrical signals produced by conventional lawnmower or outboard motor ignition systems, which generally produce an oscillating output voltage of between 4,000–20,000 volts, could be used. The lead from the ignition circuit is applied to the bite victim very quickly and then removed, so that the victim receives a sharp pulse of current. This may be done 3 or 4 times, at intervals of several seconds.

The use of a capacitor in a discharge circuit is also a possibility. For instance, a 12 volt battery has been used in combination with a coil, or a magneto can be used in combination with a capacitor which stores the charge and then is discharged into the bite area. Further, a piezoelectric element could be used to produce the required signal.

Also, an apparatus known generically as a stun gun, which is commercially available, has been successfully used. The stun gun circuit typically includes an oscillator/low voltage transformer circuit which provides a high voltage signal which is then rectified and stored in a capacitor. The stored charge is then dumped into a high voltage transformer, which produces an open circuit voltage of 50 kilovolts. When applied to a patient, this voltage will produce an approximately 6 mill lamp current spike. The electrical output is thus in the form of successive signal "bursts", controlled by the trigger of the gun. The significant advantage of the stun gun is that it operates off a conventional 9 volt battery, and is readily portable. The gun can be readily modified to include the ground plate, as shown in FIG. 2.

FIG. 3 is a simplified block diagram showing a circuit similar to the stun gun arrangement which produces a high output voltage at relatively low current, i.e. 50 kv at less than 10ma, depending upon the specific current components used.

Referring now to FIG. 3, the circuit shown is powered by a conventional battery 20, preferably a 9 volt nickel cadmium battery. The 9 volt battery is connected to the primary of a transformer 22, referred to as a low voltage transformer, through transistors 24 and 26. Generally, when the battery voltage is applied, the flux in the primary of the transformer increases and the two transistors 24 and 26 begin to oscillate, with the transistors alternately applying voltage to the respective primary windings 21 of the transformer.

The resulting signal produced in the secondary 30 of transformer 22 will be increased by a factor of 50 relative to the primary voltage in the embodiment shown since the transformer 22 has a 1 to 50 turns ratio. The signal across the secondary winding 30 will then be applied through a rectification circuit comprising diodes 32-35, charging capacitor 36. Typically, capacitor 36, which in the embodiment shown has a value of 1 microfared, will charge to approximately 1,000 volts. At this voltage level, the atmosphere in spark gap 38 will become ionized and the spark gap will conduct, allowing current to flow in the primary winding 40 of high voltage transformer 42.

High voltage transformer 42 in the embodiment shown also has a turns ratio of 1 to 50. The resulting signal across the secondary winding 44, between output lines 46 and 48, will thus be approximately 50,000 volts. This output signal may be then applied to the site of the venomous bite by conventional leads and probes (not shown).

As the capacitor 36 completes its discharge, the current through the spark gap terminates, and the signal between lines 46 and 48 decays on an exponential basis. Although the signal at secondary winding 44 is not a true sinusoid, it has been found to be effective.

As pointed out above, a high voltage signal is used to insure a current through the limb or body of the victim, in the area affected by the venom. However, if through the use of saline solutions or gels or other means, a current into the affected area can be assured at relatively low voltages, high voltages are not necessary.

Figure 4:
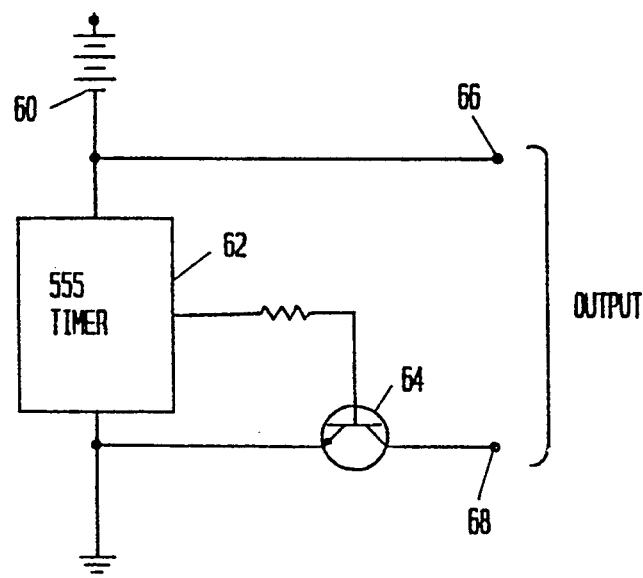
FIG. 4 is a simplified electrical diagram of another embodiment of the electric current generating portion of the apparatus of the present invention.

FIG. 4 illustrates a simple circuit which produces a relatively low voltage pulse output, at a selected frequency. The battery 60 provides a 9 volt DC input to a conventional integrated circuit timer 62, the output of which is connected to a transistor 64. The output voltage developed at points 66 and 68 may be applied through conventional leads to the bite site, The output signal has a frequency determined by the timer 62. The frequency could in some cases be relatively high, on the order of 20 khz, which may reduce the pain to the patient caused by the application of the electrical signal. In this embodiment, the actual output voltage is relatively low, on the order of 15 volts.

Hence, it should be understood that various circuits can be used to provide the required electrical current, although there is a significant advantage to an apparatus which is portable. It should be understood also that the characteristics of the electrical signal can be varied, although as indicated above, the voltage must be sufficient to establish the current through the body. Typically in a given treatment, the circuit is activated four or five times, so that there is a pattern of discharge and signal decay several times for a particular treatment.

Although the embodiment illustrated includes a point probe in combination with an opposed grounding plate, it is possible as mentioned above to use opposed points, and in certain cases just one probe which contains two electrodes. Also, while the current is usually applied to the actual site of the bite, in certain cases, the current can be applied to a point remote from the bite or the signal could be applied through the entire body.

It has been found by the applicant that use of the point/plate embodiment is substantially uniformly successful if applied within a relatively short time, i.e. 45 minutes, following the bite. In such a case, there is relief of pain from the snakebite, without any long term toxic effects and no tissue damage. At longer intervals, i.e. approximately 2 hours, particularly for highly toxic snake bites, it may be desirable to apply the current through the entire body instead of at the site of the wound, since the venom will have by that time dispersed from the site.

As indicated above, the treatment is also effective in treatment of bacterial toxins, such as found in boils, although several days are usually necessary for complete recovery. The treatment also can be used to treat other toxins, including man-made, which are present in a patient.

As indicated above, if treatment is initiated early enough, there will be substantially no reaction to the snake bite or other venomous bite. Even where certain symptoms have already appeared, further effects of the venom is terminated. Although it is believed that the electrical current has an effect on the venom itself, physiological effects on the bite victim may also play an important part. For instance, the electric current may restrict circulation in the affected area, or it may alter the molecular structure of the toxin, rendering it harmless and/or evoke a physiological reaction or response in the body which interrupts the normal action of the toxin.

Hence, an apparatus and method has been described for the prompt, effective treatment of venomous bites. The technique is effective on both humans and animals. The invention basically involves the application of an electric current into the body portion affected, i.e. typically the site of the bite. Various circuits and techniques have been developed to employ the basic concept.

Although a preferred embodiment of the invention has been disclosed herein for purposes of illustration it should be understood that various changes, modifications and substitutions may be incorporated in such embodiment without departing from the spirit of the invention as defined by the claims which follow.

I claim:

1. A toxin treatment apparatus for use against toxin present in an affected area of a body, wherein the affected area of the body is at least partially in the vicinity of a penetration of the skin of the body through which the toxin is introduced into the body, comprising:

means for generating an electrical signal having sufficient voltage to overcome the resistance of the skin of the body and to produce a current in the body through the affected area; and means connected to the electrical signal generating means for applying the electrical signal to the body, wherein said applying means includes first and second elements for contacting the body, said first and second elements being adapted, spaced and configured relative to the affected area of the body to insure that the current moves between the first and second elements through the affected area of the body and wherein the current moving through the affected area of the body is characterized such that the harmful effects of the toxin are substantially neutralized, wherein the first and second elements include a grounding member and a probe, and wherein the probe has a free end which is pointed and otherwise adapted to be applied to the affected area of the body containing the toxin.

2. An apparatus of claim 1, wherein said pointed free end is sharp enough to pierce the skin.

3. A toxin treatment apparatus for use against toxin present in an affected area of a body, wherein the affected area of the body is at least partially in the vicinity of a penetration of the skin of the body through which the toxin is introduced into the body, comprising:

means for generating an electrical signal having sufficient voltage to overcome the resistance of the skin of the body and to produce a current in the body through the affected area; and means connected to the electrical signal generating means for applying the electrical signal to the body, wherein said applying means includes first and second elements for contacting the body, said first and second elements being adapted, spaced and configured relative to the affected area of the body to insure that the current moves between the first and second elements through the affected area of the body and wherein the current moving through the affected area of the body is characterized such that the harmful effects of the toxin are substantially neutralized, wherein the first and second elements include a grounding member and a probe and wherein the probe has a free end which is blunt and otherwise adapted to be applied to the affected area of the body containing the toxin.

4. A toxin treatment apparatus for use against toxin present in an affected area of a body, wherein the affected area of the body is at least partially in the vicinity of a penetration of the skin of the body through which the toxin is introduced into the body, comprising:

means for generating an electrical signal having sufficient voltage to overcome the resistance of the skin of the body and to produce a current in the body through the affected area; and means connected to the electrical signal generating means for applying the electrical signal to the body, wherein said applying means includes first and second elements for contacting the body, said first and second elements being adapted, spaced and configured relative to the affected area of the body to insure that the current moves between the first and second elements and through the affected area of the body and wherein the current moving through the affected area of the body is characterized such that the harmful effects of the toxin are substantially neutralized, wherein said means for generating an electrical signal includes a source of electrical power which is a piezoelectric element.

* * * * *